United States Patent [19]

Weitz et al.

[11] 4,038,307
[45] July 26, 1977

[54] MANUFACTURE OF BUTENEDIOL DIACETATES

[75] Inventors: Hans-Martin Weitz, Frankenthal; Juergen Hartig, Ludwigshafen, both of Germany

[73] Assignee: BASF Aktiengesellschaft, Ludwigshafen, Germany

[21] Appl. No.: 572,133

[22] Filed: Apr. 28, 1975

[30] Foreign Application Priority Data

May 3, 1974 Germany .............................. 2421408

[51] Int. Cl.$^2$ .............................................. C07C 67/05
[52] U.S. Cl. ............................................... 260/497 A
[58] Field of Search .................................... 260/497 A

[56] References Cited

U.S. PATENT DOCUMENTS

| 3,671,577 | 6/1972 | Ono | 260/497 A |
| 3,755,423 | 8/1973 | Onoda | 260/497 A |
| 3,922,300 | 11/1975 | Onoda | 260/497 A |

*Primary Examiner*—Lorraine A. Weinberger
*Assistant Examiner*—Michael Shippen
*Attorney, Agent, or Firm*—Keil, Thompson & Shurtleff

[57] ABSTRACT

A process for the manufacture of butenediol diacetates, especially of but-2-ene-1,4-diol diacetate, by reaction of butadiene with oxygen and acetic acid, in the gas phase, over a solid catalyst which contains palladium and at least one element of main group 5 or 6.

3 Claims, No Drawings

MANUFACTURE OF BUTENEDIOL DIACETATES

The present invention relates to a process for the manufacture of butenediol diacetates, especially of but-2-ene-1,4-diol diacetate, by reaction of butadiene with oxygen and acetic acid, in the gas phase, over a solid catalyst which contains palladium and at least one element of main group 5 or 6.

The reaction of butadiene with oxygen and acetic acid in the presence of solid catalysts containing palladium, to give butenediol diacetates, has been disclosed by DOS (German Published Application) No. 2,217,452 and DOS (German Published Application) No. 2,200,124. A disadvantage of the liquid phase method is the low rate of reaction. Further disadvantages are that undesired by-products such as 1-acetoxy-1,3-butadiene are formed and that it is necessary to carry out the reaction at a low concentration of butadiene so as not to decrease the activity of the catalyst.

It is an object of the present invention to provide a process which is technologically simpler and produces less by-products. We have found that these and other objects may be achieved by an improved process for the manufacture of butenediol diacetate, especially but-2-ene-1,4-dioldiacetate, wherein butadiene, oxygen and acetic acid are reacted over a solid catalyst which contains palladium and at least one of the elements phosphorus, arsenic, antimony, bismuth, selenium and tellurium, the improvement being that the reaction is carried out in the gas phase.

We have also found that the activity of the catalyst may be increased substantially by carrying out the reaction in the presence of carbon monoxide.

The supported catalysts may be manufactured by the conventional processes of manufacture of supported metal catalysts.

By way of example, the catalysts may be manufactured by introducing a carrier into a solution obtained by dissolving a palladium compound and one or more phosphorus, arsenic, antimony, bismuth, tellurium and selenium compounds in a suitable solvent; the solvent is then distilled off in order to deposit the above components on the carrier, after which these components are reduced in a stream of gas containing hydrogen or a reducing compound, or by means of conventional reducing agents, such as hydrazine, methanol or formaldehyde. Catalysts may also be manufactured by introducing the carrier into a solution of a palladium salt and of one or more salts chosen from amongst phosphorus, arsenic, antimony, bismuth, tellurium and selenium salts, then adding a precipitant such as an alkaline reagent, eg. an alkali metal hydroxide, to precipitate these components on the support, and thereafter reducing the product by the above process. Palladium and antimony, phosphorus, arsenic, bismuth, tellurium and selenium may be deposited on the carrier either simultaneously or successively.

Any process of reduction which reduces palladium and arsenic, antimony, bismuth, tellurium and selenium to the metals may be employed. In general, the catalyst is treated with the gaseous reducing agent at from 100° to 500° C.

The choice of the palladium compound used to manufacture the catalyst is not critical though cost reasons suggest a palladium halide, such as palladium chloride, a salt of an organic acid, such as palladium acetate, or palladium nitrate, palladium oxide and the like. However, other palladium compounds, eg. sodium palladium chloride, sodium palladium sulfate and the like may also be used.

As a rule, the concentration of palladium on the carrier is from 0.1 to 20 percent by weight, through both higher and lower concentrations are feasible.

There are also no particular restrictions imposed on the arsenic, antimony, bismuth, tellurium and selenium compounds used as the further components for the manufacture of the catalysts; halides, nitrates, sulfates, oxides and other such compounds may be used. Suitable compounds containing phosphorus include ortho-phosphoric acid, meta-phosphoric acid, alkali metal phosphates, alkaline earth metal phosphates and the like.

Though the phosphorus, arsenic, antimony, bismuth, tellurium and selenium compounds deposited on the carriers are active within a broad range of concentrations, it has in general been found suitable to use from 0.05 to 30 percent by weight, in particular from 0.05 to 15 percent by weight.

Carriers such as active charcoal, silica gel, silicic acid, alumina, clay, bauxite, magnesia, kieselguhr, pumice and the like may be used to manufacture the catalyst. The carriers may be activated by conventional methods, eg. by treatment with acids. The use of active charcoal is preferred.

The reaction according to the invention may be carried out continuously or batchwise by any conventional gas phase process, eg. using a fixed bed, fluidized bed or the like.

The carbon monoxide used to improve and/or prolong the activity of the catalyst may be fed in continuously or batchwise. Eg., butadiene, oxygen and acetic acid may be reacted by passing them over the catalyst and adding carbon monoxide to the feed mixture at certain intervals. However, carbon monoxide by itself may also be passed over the catalyst to regenerate it. Further, carbon monoxide may be added continuously to the gaseous feed mixture. The amounts of carbon monoxide employed are in general from 0.01 to 25 percent by volume, preferably from 0.1 to 10 percent by volume, based on butadiene employed.

The reaction temperature is in general from 100° to 180°, preferably from 120° to 150°. The reaction pressure is decided by the procedure used and is in general from atmospheric pressure to about 100 atmospheres.

But-2-ene-1,4-diol diacetate, which may be manufactured by the process of the invention, is a valuable intermediate for the manufacture of butenediol and butanediol.

The examples which follow are intended to explain the invention in more detail without implying any limitation.

EXAMPLE 1

250 mmoles (44.5 g) of palladium chloride and 32.5 mmoles (5.2 g) of tellurium dioxide were dissolved in 2,000 ml of 6 N hydrochloric acid; 500 g of active charcoal (4 mm $\phi$) were added and the mixture was slowly evaporated to dryness on a waterbath. After further drying by passing a stream of nitrogen gas at 150° for 2 hours through the catalyst in a tube, the material was reduced by passing a stream of nitrogen gas, saturated with methanol at room temperature, through the tube at a rate of 5l/min for 10 hours at 200° C and 3 hours at 400° C.

370 ml (144 g) of the catalyst obtained were packed into a jacketed tube ($\phi$ 32 mm; L = 50 cm). Per hour, 10.5 l (S.T.P.) of butadiene, 10.5 l (S.T.P.) of oxygen and 250 ml of acetic acid were fed in at 130°. The acetic acid was fed in as vapor, having been heated to 130° in a vaporizer.

Samples were taken hourly and worked up by distillation. Analysis of the distillate showed that it contained more than 99% of butenediol diacetate. The space-time yields after 4, 11 and 32 hours are shown in the table.

| Time (hrs) | 4 | 11 | 32 |
|---|---|---|---|
| g of BEDA/kg of catalyst . hr | 57.1 | 59 | 50 |
| g of BEDA/l of reaction space . hr | 22.5 | 23 | 19.5 |
| BEDA = But-2-ene-1,4-diol diacetate | | | |

EXAMPLE 2

The reactor was filled with catalyst analogously to Example 1. Per hour, 10.5 l (S.T.P.) of butadiene, 10.5 l (S.T.P.) of oxygen, 1 l (S.T.P.) of carbon monoxide and 250 ml of acetic acid were fed in at 130°. After working up as in Example 1, the following space-time yields were found.

| Time (hrs) | 4 | 11 |
|---|---|---|
| g of BEDA/kg of catalyst . hr | 98 | 96 |
| g of BEDA/l of reaction space. hr | 43 | 42 |

COMPARATIVE EXPERIMENT
(Example 14 of DOS (German Published Application No. 2,200,124)

10 g of a catalyst containing 1.0 percent by weight of palladium and 3.0 percent by weight of potassium acetate on aluminum oxide, of surface area 30 m²/g, are introduced into a hard glass reaction tube in 10 mm internal diameter. A gaseous mixture of 1,3-butadiene, acetic acid and oxygen in the volume ratio of 70:20:10 is then passed continuously, at 130° C and atmospheric pressure, through the reaction tube, at a flow rate of 3 l per hour. The reaction takes place under these conditions.

1,4-Diacetoxy-2-butene, 3,4-diacetoxy-1-butene and 1-acetoxy-1,3-butadiene are formed respectively at a rate of 25, 2.5 and 13 g per l of catalyst per hour; the off-gas contains 1.0 percent by volume of carbon dioxide.

We claim:

1. In an improved process for the manufacture of butenediol diacetates by reacting butadiene with oxygen and acetic acid over a solid catalyst which contains palladium and at least one of the elements selected from the group consisting of phosphorus, arsenic, antimony, bismuth, selenium and tellurium, the improvement which comprises carrying out the reaction in the gas phase in the presence of carbon monoxide.

2. A process as set forth in claim 1 wherein the amount of carbon monoxide is from 0.01 to 25% by volume based on the amount of butadiene.

3. A process as set forth in claim 1 wherein the amount of carbon monoxide is from 0.1 to 10% by volume based on the amount of butadiene.

* * * * *